(12) United States Patent
Yang

(10) Patent No.: US 11,504,323 B2
(45) Date of Patent: Nov. 22, 2022

(54) BOUNDARY SURFACE CHARGED CONTACT LENS FOR DELIVERY

(71) Applicant: Lynthera Corporation, Lancaster, PA (US)

(72) Inventor: Arthur Jing-Min Yang, Bethesda, MD (US)

(73) Assignee: Lynthera Corporation, Lancaster, PA (US)

( * ) Notice: Subject to any disclaimer, the term of this patent is extended or adjusted under 35 U.S.C. 154(b) by 0 days.

(21) Appl. No.: 17/654,963

(22) Filed: Mar. 15, 2022

(65) Prior Publication Data

US 2022/0192975 A1 Jun. 23, 2022

Related U.S. Application Data

(63) Continuation of application No. PCT/US2021/072779, filed on Dec. 7, 2021.

(60) Provisional application No. 63/123,237, filed on Dec. 9, 2020.

(51) Int. Cl.
| | |
|---|---|
| *A61K 31/196* | (2006.01) |
| *A61K 9/00* | (2006.01) |
| *A61K 47/12* | (2006.01) |
| *A61K 31/445* | (2006.01) |
| *A61K 31/245* | (2006.01) |
| *A61K 47/32* | (2006.01) |
| *A61K 47/18* | (2017.01) |
| *A61K 47/24* | (2006.01) |
| *A61K 31/4535* | (2006.01) |

(52) U.S. Cl.
CPC .......... *A61K 9/0048* (2013.01); *A61K 31/196* (2013.01); *A61K 31/245* (2013.01); *A61K 31/445* (2013.01); *A61K 31/4535* (2013.01); *A61K 47/12* (2013.01); *A61K 47/18* (2013.01); *A61K 47/24* (2013.01); *A61K 47/32* (2013.01)

(58) Field of Classification Search
None
See application file for complete search history.

(56) References Cited

U.S. PATENT DOCUMENTS

| 2019/0224045 A1 | 7/2019 | Yang et al. |
| 2020/0206030 A1 | 7/2020 | Yang et al. |

FOREIGN PATENT DOCUMENTS

| WO | 2021/011670 A1 | 1/2021 |
| WO | 2021/211670 A1 | 10/2021 |

OTHER PUBLICATIONS

International Search Report and Written Opinion of the International Searching Authority for Application No. PCT/US2021/072779, dated Feb. 23, 2022 (9 pages).

*Primary Examiner* — David J Blanchard
*Assistant Examiner* — Daniel F Coughlin
(74) *Attorney, Agent, or Firm* — Perkins Coie LLP; Viola T. Kung

(57) ABSTRACT

The present invention relates to a delivery contact lens device for delivering cargo molecules. The device comprises cargo molecules and a nanocomposite comprising hydrophilic polymer domains, hydrophobic polymer domains, aqueous pores, and charged boundary double layers, wherein at least 80% of the cargo molecule partitions in the charged boundary double layers formed at the interface of (i) aqueous pores and (ii) either hydrophobic polymer domains or hydrophilic polymer domains, the charged boundary double layers have a surface charge density of 0.005 to 0.5 Coulomb/meter$^2$, and the aqueous pores including the cargo molecules have a low ionic strength of 0.1 to 100 mM, and osmolarity of 200-300 mM. The device retains the cargo molecules within the contact lens in a storage mode under a low ionic strength condition and releases the cargo molecules immediately after being placed in a tear environment with a higher ionic strength.

19 Claims, 16 Drawing Sheets

Summary diagram of contact lens device application

A contact lens delivery device with high-precision delivery of cargo from low to higher ionic strength when placed in contact with tear film.

BOUNDARY SURFACE CHARGED CONTACT LENS FOR DELIVERY

This application is a continuation of PCT/US2021/072779, filed Dec. 7, 2021; which claims the benefit of U.S. Provisional Application No. 63/123,237, filed Dec. 9, 2020. The contents of the above-identified applications are incorporated herein by reference in their entirety.

FIELD OF THE INVENTION

This invention relates to a nanoengineered contact lens device prepared for the delivery of pharmaceutical or non-pharmaceutical cargos immediately after being placed in contact with an ocular tear environment with precisely the prescribed daily dosage for an extended period (more than a week). The deliverable ingredient(s) are impregnated within a contact lens device comprising aqueous pores, embedded within one or more type of hydrophilic domains, one or more type of hydrophobic domains, of which some or all domain-pore boundaries are modified with charged double layers. The boundary charge double layers provide the engineered option to precisely control the timing and kinetics of the cargo delivery.

BACKGROUND OF THE INVENTION

The silicone-hydrogel composite technology, since its implementation in 1997, has improved both the water affinity and oxygen permeability of a contact lens and transformed it into a breathable and hydrophilic soft tissue-resembling device. Polymers of 2-hydroxyethyl methacrylate (HEMA) and silicone-containing polymers incorporated in the device can be utilized as a reservoir to store drugs of similar hydrophilic lipophilic balance. U.S. Pat. No. 10,617,559 discloses a device comprising: (i) at least a drug, (ii) one or more reservoir domains, and (iii) a barrier domain of layer configuration (or a barrier layer) to block the drug diffusion paths from the reservoir domain to the ocular surface in the subject's eye.

Prior arts show that there are three transport modes of a drug's permeation through a porous composite. These results had shown that, after immersing a lens into a tear sink, a burst release from the dissolved drugs in aqueous pores of contact lens occurred within a few hours. The second mode of release, primarily from drugs adsorbed at the domain-pore interfaces, lasted for more than a day. The drugs entrapped within the solid polymeric domain came out the slowest and the timing could be sustained for many weeks depending on the solid polymer's relaxation time scale (related to the polymer's glass transition temperature) and the drug's solubility in tears.

Many attempts of using CL for extended ocular drug delivery failed due to the sudden burst release of the majority payload within a few hours. Many efforts in the field have been devoted to the developing a practical contact lens (CL) delivery device which releases less than 20% in the first day while preserving the majority (80%) of the deliverable payload to be gradually discharged throughout the intended long duration of more than a week. These approaches included the use of a barrier coating, a dissolved diffusion barrier, charged surfactants, or nanocarriers, etc. to lower down the burst release.

There exists a need for a sophisticated contact lens delivery device that discharges a cargo only after the device is placed in contact with ocular tear film.

Release in PBS at different pH values (5.5, 6.4, and 7.4). Dailies Total 1® contact lenses.

Figure 31:
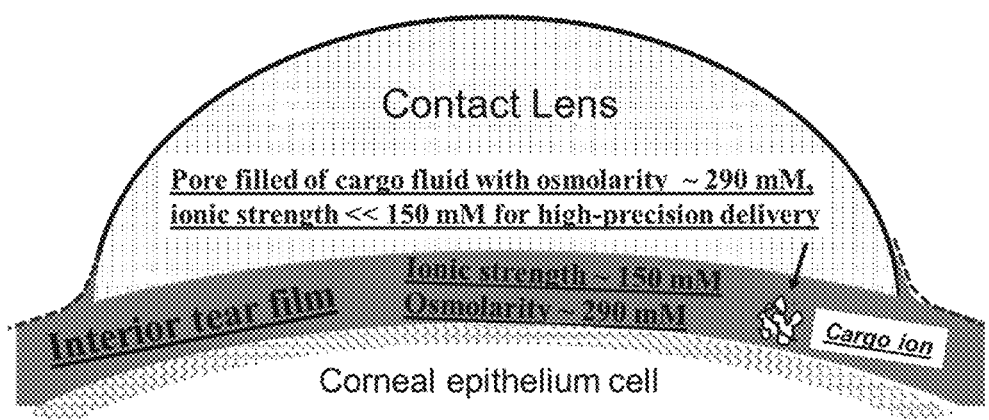

FIG. 31 Summary diagram of present contact lens device application

DETAILED DESCRIPTION OF THE INVENTION

Definitions

A "cargo molecule" is a pharmaceutical or non-pharmaceutical compound deliverable to the ocular system for a function of curing ocular diseases or improving health. For example, a cargo molecule can be a drug, a vitamin, or a nutrient.

A "delivery contact lens" (DCL) as used herein, refers to a transparent lens device that is in contact with a tear film, on top of cornea, for the purpose of delivering a pharmaceutical, or a non-pharmaceutical cargo compound into the ocular environment.

A "drug" or "pharmaceutical compound" as used herein, refers to a molecule having an activity to cause a physiological change in a subject, such as a pharmaceutical drug or an essential nutrient.

A "charged drug or cargo compound" means their molecules are either cationic or anionic under the normal physiological conditions. They can be among the class of compounds having a pKa, pKb, or an isoelectric point, which include, but not limited to, proteins, small peptides, molecules with other Lewis acid or base groups.

A "hydrophobic/hydrophilic" ratio is a measure of a material's hydrophobicity based on its solubility and partition between hydrophobic octanol and hydrophilic water. It is normally referred to a material constant logP of octanol/water, where P is a partition coefficient ratio of a soluble component between octanol and water (Sangster J, J Phys Chem Ref Data 1989;18: No. 3). A high logP value means hydrophobic and a low or negative value means hydrophilic.

A "junction potential" is a Coulomb potential resulted from the self-diffusion of electrons or ions at the boundary of a conductor, semiconductor, or electrolyte solution. Examples are metal couple junction, P-N junction, liquid junction, or cell-membrane aqueous medium junction.

A "boundary charged double layer", as used herein in the present device, consists of a pair of negatively charged layer and a positively charged layer, and is formed at the boundary interface of the hydrophilic or hydrophobic polymer domains with the covering aqueous water pores in DCL. The boundary charged double layer often consists a surface Stern layer and a diffusive Debye layer like those of a colloidal particle or an ionic crystal. For example, the boundary charges double layer can be formed from the charges of a head group of a boundary charge modifier, and the opposite charges of the cargo species or other counterions to the charged head groups.

A "boundary charge modifier" is a compound implanted onto a water-polymer interface, either by physical dissolving or chemical bonding, to create a boundary charged double layer on the water-polymer domain interface and a junction potential through interfacial ion dissociation or exchange in an aqueous medium while permanently residing at the boundary with a negligible dissolution into pore water. Such boundary charged double layer is composed of the implanted surface charges as well as the neutralizing cargo counterions, in a surface Stern layer and a diffusive Debye layer, resembling those charge double layers often observed in the colloidal systems.

A "interfacial partition coefficient" of a cargo specie is the ratio of the cargo molecular concentration in the boundary interfacial zone to the cargo's concentration in the pore fluid at an equilibrium condition.

A "boundary surface charged contact lens" is an ocular contact lens with the boundary charges immobilized at the polymer-pore interfaces, either by physical entrapment, or chemical attachment, to maintain a boundary charged double layer and consequently a junction potential at the polymer-pore interfaces within the lens whereas the interfacial charge double layer is utilized to trigger and control the release of the charged cargo species.

A "transparent nanocomposite" is a composite of multiple components with a different degree of hydrophilicity/hydrophobicity which are dispersed uniformly at the dimension magnitudes smaller than the wavelength of visible light to minimize light scattering caused by differences in refractive indexes among various domains (of pores and components). The domain morphology and size are often controlled in correlation with the degree of differences in the components' refractive indexes.

A "Bronsted-Lowry Acid/Base" of which an acid is a proton donor, and a base is a proton acceptor; the strength of an acid or base is correlated with its tendency to donate or accept protons, respectively, often measured by the proton dissociation/association constant of Pka. (Reference: The Bronsted-Lowry Acid-Base Concept, George B. Kauffman, Chem. Educ. 1988, 65, 1, 28)

Figure 1:
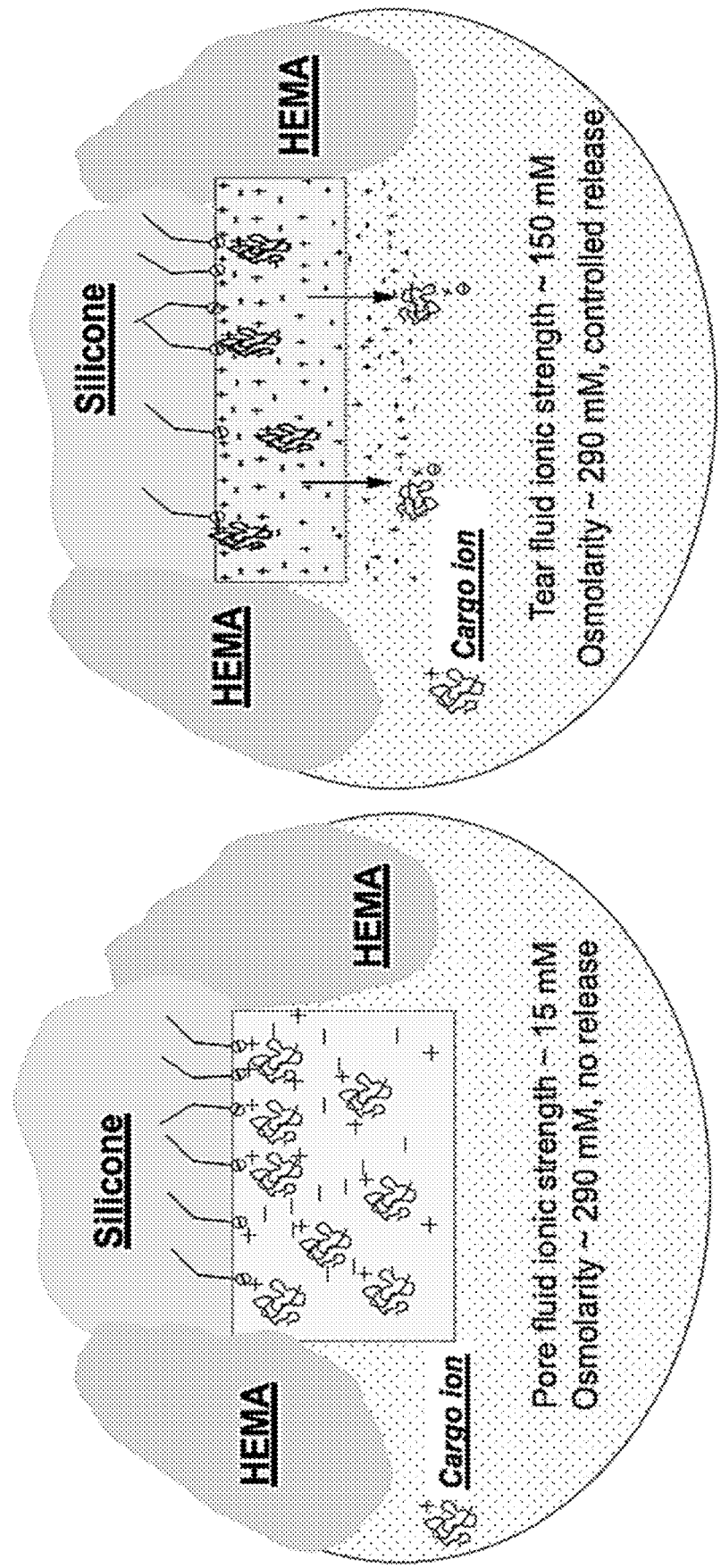
FIG. 1 Illustration of the change in double layer thickness (~3 times thinner) and accelerating release in response to a change in ionic strength from 15 mM to 150 mM.

This disclosure describes both the preparation of a porous nanocomposite with an adequate water affinity, ion and gas permeabilities and a device delivery application thereof in which the delivery of a cargo specie is controlled by utilizing the electrostatic forces between the charges implanted on the pore-polymer interfaces (interphase boundary charges layer) and those opposite charges of the cargo molecules. The boundary charge double layers formed by the immobilized boundary charge modifiers and the electrostatically adhered, oppositely charged deliverable ingredients are engineered to enrich the cargo molecules' partition in the interfacial boundary layers in loading as well as to create a retain/release mechanism in response to the change of the double layer thickness with respect to variations of the ionic strength in a contact environment. This engineered release mechanism retains cargo molecules within the contact lens in a storage mode under a low ionic strength condition (0 to 100 mM) and releases the cargo molecules immediately after being placed in a tear environment with a higher ionic strength (110~150 mM) through the ion exchange process with the tear film, for triggering as well as slowing down the burst release. (FIG. 1)

The present invention uses a built-in triggering mechanism to control a cargo discharge only after the device is placed in contact with ocular tear film, and thus, simultaneously eliminate the cargo's premature discharge in a storage medium, thereby allowing a more sophisticated control of both the burst release of cargo molecules and premature loss in storage medium during the long shelf-life. The present invention provides on-demand delivery of the cargo molecules into an ocular tear film for an extend duration of one day to one month whenever the device, after removal from storage package, is placed in contact with an ocular tear film of normal tear ionic strength. Further, the reduction of the burst release by substantially enhanced partition and the primary delivery of the cargo molecules from the interfacial charge double layers provides a precise control of their release kinetics.

The present invention is directed to a contact lens device for delivering a cargo molecule to the ocular system. The contact lens device comprises cargo molecules embedded in a nanocomposite, preferably a transparent nanocomposite. The nanocomposite comprises hydrophilic polymer domains, hydrophobic polymer domains, aqueous pores, and charged boundary double layers, wherein: (a) each of the hydrophilic polymer domains and the hydrophobic polymer domains has a diameter or a shortest axis, from 5 to 50 nm to minimize light scattering, (a) the interfacial domain-pore surface area is from 5 to 500 m$^2$/g device, (b) the aqueous pore volume is 30 to 80% of the total device volume, (c) at least 80% of the cargo molecule partitions in the charged boundary double layers formed at the interface of (i) aqueous pores and (ii) either hydrophobic polymer domains or hydrophilic polymer domains, (d) the charged boundary double layers have a surface charge density of 0.005 to 0.5 Coulomb/meter$^2$, and (e) the aqueous pores including the cargo molecules have a low ionic strength of 0.1 to 100 mM, and osmolarity of 200-300 mM.

In one embodiment, the nanocomposite is a transparent nanocomposite.

In one embodiment, present contact lens device, the size of the solid polymers' domain in the nanocomposite is in the range from 5 to 50 nanometer to minimize light transmission loss to less than 2% and keep the contact lens highly transparent, and to maximize domain-pore surface area in the range from 5 to 500 meter$^2$/gram or 10-100 meter$^2$/gram.

In the present contact lens device, the cargo molecular concentration and total amount in the device, including both the majority in the interfacial charge double layer and the minority in the pore fluid, are prescribed according to each cargo's respective efficacy preference which could range broadly from nanograms (such as a low dosage drug) to milligrams (of vitamins or nutrients).

The present device is effective to deliver both pharmaceutical as well as non-pharmaceutical compounds to ocular environment with the following advantages over the existing contact lens drug delivery in following aspects:

(i) The burst release in the first day can be reduced to less than 20% of the total delivery due to the higher partition of cargo molecules in the double charge layer in the boundary charge modified interfacial zone.

(ii) The delivery device can automatically start the cargo release on demand when it is placed in contact with an aqueous fluid having an ionic strength at least 110 mM (e.g., a tear film of ionic strength of 150 mM) due to the shrinkage of the interfacial double layer zone of a lower ionic strength (for example, the layer thickness in pore fluid of ionic strength at 15 mM is three times thicker than that in 150 mM ionic strength).

(iii) The total capacity of drug loading per device can be precisely prescribed by adjusting a device's aqueous porosity, total surface area, surface charge density, and interfacial double charge layer thickness (inversely proportional to the square root of the pore fluid's ionic strength) so that the kinetics of cargo delivery is precise and consistent within the whole delivery duration. Moreover, the precise loading capacity and release kinetics allow the device to be prepared for containing just the right amount for the intended delivery time without overloading It is important to maintain the pore and storage fluid at a low ionic strength between 0.1-100 mM, preferably 1-100 mM, or 5-50 mM, (for example, 15 mM), to allow the on-demand delivery to be triggered by ionic exchange with a tear fluid (at the higher 150 mM ionic strength) while maintaining the osmolarity of pore fluid similar to the tear osmolarity to minimize potential discomfort from changes in ocular osmotic pressure. (FIG. 1) The pore osmolarity is in general 200-300 mM, preferably 250-300 mM or 280-300 mM. It is undesirable to have a higher osmolarity such as 330 mM in pores of the device, because such high osmolarity will cause dry eye syndrome. The low ionic strength and 200-300 mM osmolarity can be achieved by adding charge-neutral, hydrophilic, non-ionic, tear-friendly compound molecules such as glycerol, polyethylene glycol (PEG), polyvinylpyrrolidone (PVP), glycoside, and carboxymethylcellulose.

Because of the long-range nature of the Coulomb forces and the pores' nanometer dimensions, the attractive forces between the surface implanted charges to the oppositely charged cargo species are the predominant interactions within a nanopore composite. We can use these attractive forces to raise the interfacial cargo population to over 80% of the total loading (i.e., less than 20% of loaded cargo remains in the bulk pore fluid) and subsequently, by modulating just this single interfacial mode discharge, we can control the most dominant and representative kinetic rate in the CL for extending the cargo release. In examples given later, our studies had shown the effective extension of a drug release duration to 50 folds longer with enhanced interfacial retention by charge interactions. We further disclose how to utilize the thickness of these interfacial ionic double layers to precisely control the delivery rate, and to build in a triggering mechanism to spontaneously initiate a DCL cargo release when the device is placed in contact with the tear film above a cornea.

By physically or chemically changing the polymer-pore boundary layers of a DCL with functional groups of charges opposite to a deliverable cargo specie, we can substantially increase the interfacial loading of cargo molecules by electrostatic Coulomb attractions so that the kinetics of cargo delivery is precise and consistent within the whole delivery.

Contact Lens Composite Materials

The hydrophilic polymer domain and hydrophobic polymer domain of the present contact lens device are made from hydrophilic components and hydrophobic components. In one embodiment, one component of the contact lens composite is elected from any of the hydrophilic components listed in Table 1A, 1B, to raise the device's water affinity and the other component is selected from any of the hydrophobic components listed in Table 1A, 1B. A nanocomposite contact lens can be made from these acrylic oligomers, or prepolymers by a thermal curing (100° C. -120° C.) process.

TABLE 1A

Common materials used to make hydrogel soft contact lens

| Hydrophilic component | Hydrophobic component |
|---|---|
| 2-Hydroxyethyl methacrylate ("HEMA") | Methyl methacrylate ("MMA") |
| N,N-dimethylacrylamide ("DMA") | Isobutyl methacrylate |
| N-vinyl-2-pyrrolidone ("NVP") | Pentyl methacrylate |
| 4,4-Dimethyl-2-vinyl-2-oxazolin-5-one | Cyclohexyl methacrylate |
| Methacrylic acid ("MAA") | Lauryl methacrylate |
| N-(Hydroxymethyl)acrylamide | |
| N-[3-(Dimethylamino)propyl] methacrylamide | |
| Ethylene glycol dimethacrylate | |

TABLE 1B

Common materials used to make silicone-hydrogel soft contact lens

| Hydrophilic component | Hydrophobic component |
|---|---|
| 2-Hydroxyethyl methacrylate | 3-[Tris(trimethylsiloxy)silyl]propyl methacrylate ("TRIS") |
| N,N-dimethylacrylamide | |
| N-vinyl-2-pyrrolidone | 3-Methacryloxy-2-hydroxypropoxy (propylbis(trimethylsilyloxy)methylsilane ("SIGMA") |
| 4,4-Dimethyl-2-vinyl-2-oxazolin-5-one | |
| Methacrylic acid | Fluorosiloxane macromer |
| 2-(Methacryloyloxyethyl)-2-(trimethylammonioethyl) phosphate | Mono-(3-methacryloxy-2-hydroxypropyloxy)propyl terminated, mono-butyl terminated polydimethylsiloxane |
| Ethylene glycol dimethacrylate | |
| Poly(N-vinyl pyrrolidone) ("PVP") | Mono-methacryloxypropyl terminated polydimethylsiloxane |
| Triethyleneglycol dimethacrylate | |

In another embodiment, the hydrophilic component can be selected from a monomer, oligomer, or prepolymer with a logP<1 that contains at least one hydrophilic group of hydroxyls, alkyl glycol, amine, lactam, carboxylic, or sulfonic group. The hydrophobic component can be composed of monomer groups with a logP>3, wherein the monomer comprises one or more hydrophobic groups selected from the group consisting of: alkyl group, aromatic group, ester group, perfluoroalkyl group. These non-compatible components can be either premixed within a compatible solvent/cosolvent system, or to be pre-reacted into block copolymers before being finally cured into a uniform nanocomposite.

Contact Lens Composite Morphology and Porosity

In one embodiment, the hydrophilic polymer domains are made ten times smaller than the hydrophobic domain average size so that the hydrophobic domains are completely immersed into a continuum mixture of hydrophilic domains and aqueous pores, a morphology desirable for enhancing the composite's water affinity, contact angle and capillary infiltration.

In another embodiment, the hydrophobic domains are in an elongated needle shape, or part of an interpenetrating network with the hydrophilic phase, to enhance Dk of oxygen permeability to above 100.

In another embodiment, the porosity (40-50% by volume) is created by a solvent/cosolvent system used for uniformly mixing the two different types of polymer, followed by washing/solvent exchange process to infuse water into pores. The dimensional length and width of polymer domains and aqueous pores are adjustable with tunning the compatibility of the oligomers of different hydrophilicity by selecting an optimal combination of solvent/cosolvent followed by a controlled curing process to prevent phase segregation during the polymerization. The objective is to make a composite lens with morphological features suitable for wearing and the loading of desired boundary surface charge modifiers. The range of the morphological attributes are (a) The polymer domains have a size, the diameter, or the shortest axis (among the three principal axis of an ellipsoidal shaped domain), from 5 to 50 nanometer to achieve high optical transmission.

(b) The interfacial domain-pore surface area is from 5 to 500 $m^2$/gram to accommodate enough cargo compound for the extended delivery (c) The aqueous pore volume is 30 to 80% of the total device volume to host a low ionic strength (for example, less than 10 mM) aqueous fluid prepared for the long-term storage of the delivery device and the on-demand release of interfacial cargo molecules when the device is in contact with tear fluid of regular high ionic strength of 150 mM.

Boundary Surface Charged Contact Lens for Drug/Cargo Delivery

The present contact lens device has the following desired biomedical functions: (a) A carrier of pharmaceutical/non-pharmaceutical cargos intended for ocular caring delivery, (b) A release apparatus that controls the cargo delivery rate and precision for an extended period (1 to 30 days), (c) A built-in triggering mechanism that prevents cargo premature leaching during device's shelf storage, while starts a sustainable release after placed in contact with the ocular tear film fluid for the designed release duration (weeks to a month).

Boundary Charge Modification and Formation

In the present device, the boundary charged double layers are formed in the sequential processes of (i) implanting the boundary charge modifiers at the polymer-pore interfaces, wherein the boundary charge modifier can be a molecule having a charged head group and a hydrophobic tail which is to be immobilized, either by chemical bonding, or strong physical cohesion, to the polymer domain at the polymer-pore boundary, followed by (ii) loading the oppositely charged cargo molecules in the interfacial zone to form the binding (Stern) as well as diffusive (Debye) counterion layer. The binding forces of the boundary charge modifiers to the polymer, whether physically or chemically attached, should be sufficiently strong to prevent their leaching throughout the use life of the device (i.e., the total leaching loss to be less than a few percentage points over the device's lifetime).

A boundary charge layer can be physical incorporated at pore interface. In one embodiment, a molecule with a hydrophobic tail (for example, an octadecyl C18 or longer aliphatic chain with a high affinity to hydrophobic polymers) can be incorporated at a polymer-aqueous pore interface by a swelling process using a good solvent of the polymer. By soaking a DCL in a loading solution containing the physical boundary modifiers dissolved in a good solvent (for example, ethanol or short chain alcohol) the charged modifier molecules can permeate within a contact lens and redistribute themselves primarily at the polymer-pore interfaces such that their hydrophobic segments attached to the polymer domain with the charged head groups fully immersed into the aqueous pore through aqueous hydration.

A boundary charge layer can also be chemically incorporated at pore interface. In one embodiment, the charged head groups are created by a chemical surface modification reaction during or after the CLs' fabrication process, like many chemical surface modification procedures employed by the art of making a porous nanocomposite. In another embodiment, a copolymeric silicone surfactant (m.w. 10,000 Da and 5% of cationic diamine side-chain component $NH-CH_2-CH_2-NH_2$) is mixed with the silicone-hydrogel oligomers batch prior to the contact lens fabrication to create positive boundary charges. The silicone polymeric surfactant is entrapped in silicone polymer domain after the lens curing due to its high molecular weight and exposes the cationic diamine groups into the pore fluid due to the exceptional flexibility of the PDMS backbone.

The objective of physical or chemical incorporation of boundary surface charge modifier is to create boundary surface charge density in the range of 0.005 to 0.5 Coulomb/meter$^2$ for attracting oppositely charged cargo molecules in the interfacial mode delivery.

In one embodiment, the boundary charged modifier is a proton donor (e.g., a Bronsted-Lowry acid). A preferred proton donor as a boundary charged modifier is a fatty acid with a carbon chain length of 8-24, or 8-18, and one carboxylic or other acid head, and the cargo molecule is positively charged. For example, the boundary charged modifier is oleic acid, linoleic acid, α-linolenic acid, myristic acid, or stearic acid.

In one embodiment, the boundary charged modifier is a proton acceptor (e.g., a Bronsted-Lowry base). One preferred proton acceptor as a boundary charged modifier is alkyl amine, ethanolamine, or a cationic quaternary ammonium salt having a carbon chain length of 8-24 or 8-18 and an alkyl amine, ethanolamine, or quaternary ammonium head group, and the cargo molecule is negatively charged. Another preferred proton acceptor as a boundary charged modifier is sphingosine, sphinganine, or phytosphingosine, or 1,2-dioleoyl-3-trimethylammonium propane.

Partition of Charged Cargo Molecules

With the incorporation of boundary surface charges, we can control the partition of charged cargo molecules in such modified DCLs. The equilibrium distribution of a charged cargo molecule at the interfacial zone of the oppositely charged boundary surface can be exponentially increased in proportion to the static Coulomb potential exerted by the boundary surface charge according to the electrochemical potential equation shown below, where m is molality, y is the activity coefficient, z is charge number, F is the Faraday constant, $$\mu = \mu^0 + RT\ln(m) + RT\ln(\gamma) \quad \gamma = \gamma_0 e^{\frac{zF\varphi}{RT}}$$

The above equation reveals that we can utilize the electrostatic Coulomb potential to change the electrochemical potential of an ionic cargo specie and thus enhance their stability (smaller γ) as well as increasing its partition coefficient in the Coulomb attraction zone. This invention discloses a method of using the boundary surface charge density along with the ionic strength in the double layer to precisely control the partition coefficient of a charged cargo specie in the interfacial double layer zone relative to its equilibrium concentration in the aqueous pores (i.e., raising $$\frac{\gamma}{\gamma_0} \text{ by } e^{\frac{-zF\varphi}{kT}})$$

and thus, make the interfacial cargo release the most dominant mode (i.e. over 80% of total cargo payload) and eliminate the sudden burst release from pore fluid as well as the imprecision of the DCL's longer-term delivery kinetics.

Formation of the Charge Double Layers

The electrostatic Coulomb potential of a boundary-charged surface is decided by the surface charge density and the surface geometry. The charge density can be adjusted by changing the concentration of the boundary charge modifiers to be loaded at the interface. Once a desired boundary charge density is known according to the calculated Coulomb potential required for lowering the cargo's electrochemical potential at the interfacial zone, the charged cargo molecules can then be loaded to the interfacial zone by soaking a DCL in a cargo loading solution. These two processes will lead to an interfacial charge double layer with a Stern layer of chemically adsorbed counterions as well as a diffusive Debye ionic layer, both of which contains a high amount of cargo molecules due to Coulomb potential between the opposite charges. The equilibrium distribution of the cargo molecules within the DCL's pores are much higher in the interfacial zone than in the pore fluid due to their Coulomb attraction to the boundary oppositely charged modifiers. The Stern layer normally contains ions that are strongly (chemically) bonded to the boundary surface charges. The Coulomb attractions in the Stern layer are much higher than thermal energies in the order of kT, where k is the Boltzmann constant. The attraction of the surface charges to cargo molecular ions in the Debye layer is shielded by the Stern layer, and thus, is in a weaker form of physical adsorption (energy~kT).

Effect of the Ionic Strength on Double Layer Thickness (From Debye's Model)

The charge distribution in the Debye layer and the consequential screened Coulomb potential in such layer are readily calculable by solving the Poisson equation to obtain the thickness (Debye length) of the diffusive layer which directly affect the partition coefficient and release kinetics of the cargo molecules.

The equilibrium distribution of charges under a Coulomb potential φ at a temperature T is, $$\rho = n_+q - n_-q = qn\left(e^{\frac{q\varphi}{kT}} - e^{\frac{q\varphi}{kT}}\right)$$

where n is ion concentration and q the charge of an electron.

The equilibrium charge density, ρ, must satisfy the following electrostatic Poisson equation, where φ is the electrostatic potential and ε is the dielectric constant of water.

$$\nabla^2 \varphi = \frac{1}{r^2}\frac{d}{dr}\left(r^2 \frac{d\varphi}{dr}\right) = -\frac{4\pi\rho}{\varepsilon}$$

Assuming $$\frac{q\varphi}{kT}$$

is small and keeping the first expansion term of the exponential, we obtain $$\nabla^2 \varphi = -\frac{4\pi q n \left(e^{\frac{q\varphi}{kT}} - e^{\frac{q\varphi}{kT}}\right)}{\varepsilon} \approx \frac{8\pi n q^2}{\varepsilon kT}\phi$$

This equation can then be solved in the exact form as follows, $$\nabla^2 \varphi = -\kappa^2 \phi, \; \varphi = \frac{zq}{\varepsilon r}e^{-\kappa r} \text{ with } \kappa^2 = \frac{4\pi q^2}{\varepsilon kT}\sum_i z_i^2 n_i$$

Figure 2:
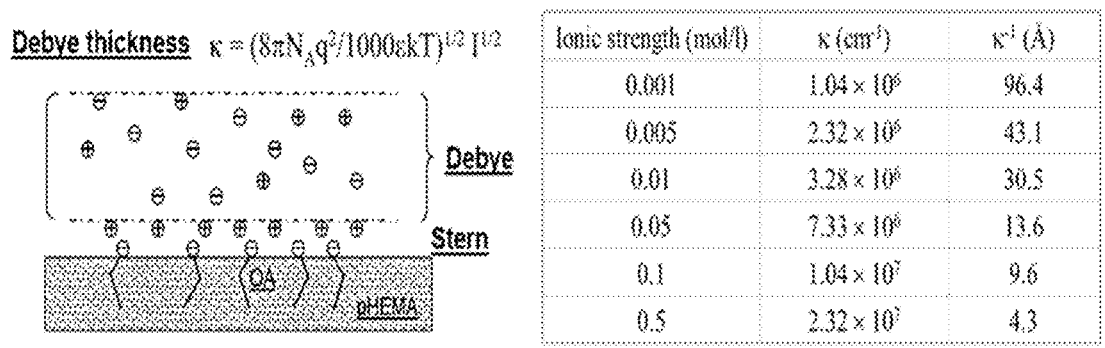
FIG. 2 Dependence of Debye layer thickness to the ionic strength of a fluid.

The above calculations had shown that the charge interaction potential, φ, at a boundary double layer was exponentially reduced by the charge shielding effect of the Debye layer of which the thickness (1/κ) is inversely proportional to the square root of ionic strength ($I^{1/2}$). This double-layer thickness can be manipulated to retain or release the interface-bounded ionic cargo species. The following table provides numerical examples for illustrating the dependence of the Debye length and layer thickness with the ionic strength in the range from 0.001 to 0.5 M. As shown a 100-fold increase in the ionic strength can reduce the layer thickness 10 times. (FIG. 2

| Ionic strength (mol/l) | κ (cm$^{-1}$) | κ$^{-1}$ (Å) |
|---|---|---|
| 0.001 | 1.04 × 10$^6$ | 96.4 |
| 0.005 | 2.32 × 10$^6$ | 43.1 |
| 0.01 | 3.28 × 10$^6$ | 30.5 |
| 0.05 | 7.33 × 10$^6$ | 13.6 |
| 0.1 | 1.04 × 10$^7$ | 9.6 |
| 0.5 | 2.32 × 10$^7$ | 4.3 |

Engineering the interfacial partition coefficient to control cargo delivery

The interfacial partition and capacity of adsorbing a charged cargo specie by boundary charged modified DCL can be readily altered to engineer a DCL device for having a high ratio of interfacial concentration to that in the pore fluid and thus substantially reducing the cargo specie's burst release from the pore fluid. The primary option is to control the loading density of the boundary charges to raise the cargo's interfacial partition higher than 80% of the total cargo loading. Secondly, the ionic strength of the cargo loading solution can also be restricted to lead to a thicker Debye layer for containing more cargo molecules in the enlarged double layer of the interfacial zone.

Stabilization and Discharge Through Changing Ionic Strength

The present invention provides a storage package comprising the present contact lens and a storage fluid having an ionic strength within 10% of the ionic strength of the aqueous pores of the device.

The present invention also provides a method of releasing cargo molecules from the above storage device. The method comprises the steps of: removing the device from the storage package, placing the device in an aqueous fluid (for example, tear) comprising an ionic strength of at least 110 mM, and releasing the cargo to the aqueous fluid triggered by the increase of ionic strength from the aqueous pores to the aqueous fluid.

The present invention provides a method to slow down or speed up the cargo's discharge rate. A unique feature of the boundary charge modified DCL is the ability of changing the interfacial layer thickness, and thus, the electrochemical potential of the cargo molecules in the double layer zone with a simple change of the ionic strengths of fluid in the pores. For instance, a boundary charge incorporated DCL can be stored in a low ionic strength medium (for example, <0.001 M) with a thick double layer (for example, ~10 nanometer) to prevent cargo molecules leaching from the interfacial layer into pore fluid. When such device is placed in contact with a normal tear fluid of ionic strength ~150 mM, the thickness of the double layer in the DCL is expected to shrink to below 1 nanometer and consequently trigger a spontaneous release in the process. With the gradual increase of the ionic strength in the CL pores through diffusion, the interfacial cargo molecules' partition coefficient is decreased due to the shrinkage of the layer thickness caused by ion exchanges between tear and storage fluid in pores. This feature can be utilized for triggering the cargo delivery when a DCL is displaced from a blister package (with low ionic strength) into contacting with the tear environment of physiological ionic strength 150 mM.

Effect of Fatty Acid Carbon Chain Length on Release Kinetics of Cationic Drugs

The interfacial charge density of a surface implanted modifier (boundary charge modifier) is correlated with the molecules' inherent charge dissociation/association constants (for examples, pKa of an acid or pKb of a base), the chain length of hydrophobic tail and the pH value of the pore fluid. The length of the hydrophobic chain has a direct impact on dissociation/association constants, but more importantly, on the modifier's solubility partition between the bulk polymer domain and pore fluid. Both impacts explicitly affect the cargo release kinetics and the later could lead to an undesired leaching of charge modifiers in extended use of the device.

Oleic acid, myristic acid, lauric acid, capric acid, and octanoic acid have an 18, 14, 12, 10 and 8-carbon chain length are illustrated below with effects on solubilities shown in the table.

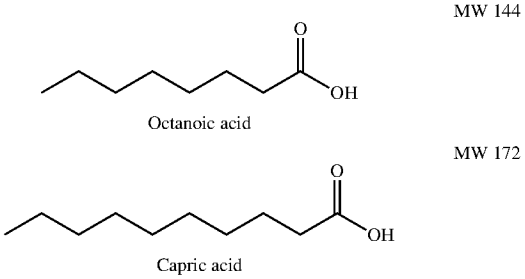

MW 144
Octanoic acid

MW 172
Capric acid

-continued

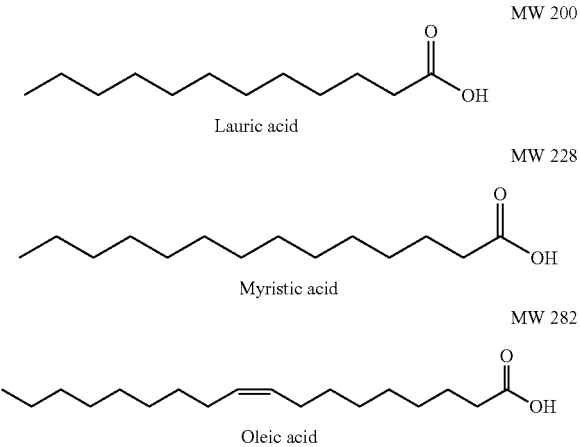

| Fatty acid | # of carbons and degree of saturation | Melting point (C.) | Solubility in water (M) |
|---|---|---|---|
| Octanoic acid | 8:0 | 16-17 | $4.7 \times 10^{-3}$ |
| Capric acid | 10:0 | 31-32 | $3.0 \times 10^{-4}$ |
| Lauric acid | 12:0 | 43-45 | $1.2 \times 10^{-5}$ |
| Myristic acid | 14:0 | 53-58 | $1.0 \times 10^{-6}$ |
| Oleic acid | 18:1;(cis)9 | 10-16 | $4.1 \times 10^{-8}$ |

The effects of fatty acid chain length on respective drug release kinetics are disclosed in examples 9 (FIGS. 21-26).

Effect of Fluid Media pH on Release Kinetics

When the pH of a fluid medium is raised or lowered by one unit, the fatty acid's dissociation into anions is changed by a factor of ~10 according to the equilibrium equation of pKa. Such a change in the fatty acid's dissociation rate will proportionally affect the surface charge density at the interface and consequently on the drug's electrochemical potential as well as its release kinetics from a contact lens.

The following examples further illustrate the present invention. These examples are intended merely to be illustrative of the present invention and are not to be construed as being limiting.

EXAMPLES

Example 1. Loading Oleic Acid (OA) Into Silicone Hydrogel Commercial Contact Lenses This example illustrates incorporation of boundary surface charge modifiers by a swelling process.

In this example, the anionic fatty acid is loaded into the silicone polymer domain of a silicone-hydrogel contact lens by a swelling process using a good solvent such as ethanol. The device is a commercial silicone hydrogel, ACUVUE Oasys® contact lens (Johnson & Johnson Vision Care, Inc., Jacksonville, Fla.) and the fatty acid is oleic acid. This lens consists HEMA hydrophilic polymer, silicone hydrophobic polymer and has 38% water content in aqueous pores. Ethanol is a good solvent that can swell the silicone phase.

The silicone hydrogel commercial lenses were rinsed with deionized water and then air-dried before use. ACUVUE Oasys® contact lenses were soaked in 4 mL of 19 mg/mL or 33 mg/mL of oleic acid in ethanol. ACUVUE TruEye®, silicone hydrogel contact lenses, were soaked in 4 mL of 19 mg/mL, 27 mg/mL or 40 mg/mL of oleic acid in ethanol. The soaking duration was 24 hours at room temperature. Following the loading step, the contact lenses were taken out and excess fatty acid-ethanol solution was blotted out from the lens surface, and the lens was air-dried overnight. The loading amount of OA was determined by weighing the dry lens before and after the fatty acid loading period.

Example 2. Loading Oleic Acid (OA) Into Pristine Conventional Hydrogel pHEMA Contact Lenses In this example, the contact lens device is a HEMA 1-day ACUVUE Moist® contact lens and the fatty acid is oleic acid. Methanol is a good solvent for swelling but not good for processing because minor residual could be harmful to the eyes. Due to the negligible swelling of conventional hydrogel pHEMA lenses in ethanol, we alternatively developed a water/ethanol solvent mixture that can swell the HEMA phase.

Lenses were rinsed with PBS and then air-dried before use. Dry lenses were soaked in 4 mL of 100 mg/mL of oleic acid in a mixture of ethanol and deionized water (75/25 ethanol/water). Following the loading step, the contact lenses were taken out and excess fatty acid-ethanol solution was blotted out from the lens surface. Lenses were washed in PBS for 1 hour and then were air-dried overnight. The loading amount of OA was determined by weighing the dry lens before and after the fatty acid loading period.

In example 6, we used the same swelling process to load cationic boundary surface charge modifiers including sphingosine, sphinganine, phytosphingosine, and 1,2-dioleoyl-3-trimethylammonium propane (DOTAP) respectively into TruEye® contact lenses.

The drug release experiments in following examples were normally carried out by soaking the drug loaded lenses in 3 mL of release medium. During the release experiments, 1 mL of release sample was removed at predetermined time intervals, and 1 mL of fresh solution was refilled into the release medium. The amount of drug released was measured using a UV-Spectrophotometer.

Figure 3:
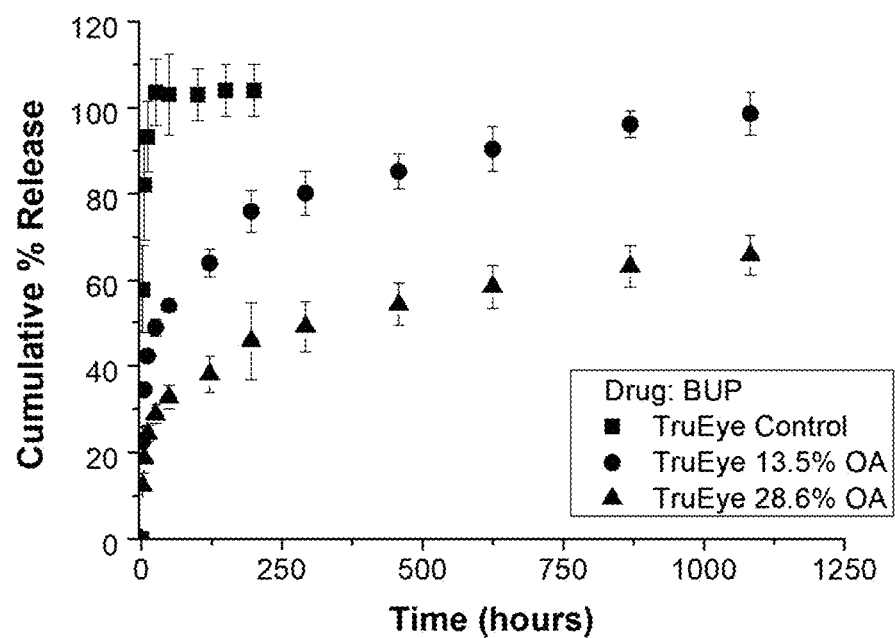
FIG. 3 Cumulative % release of BUP from contact lenses loaded with oleic acid. TruEye® contact lenses.
Figure 4:
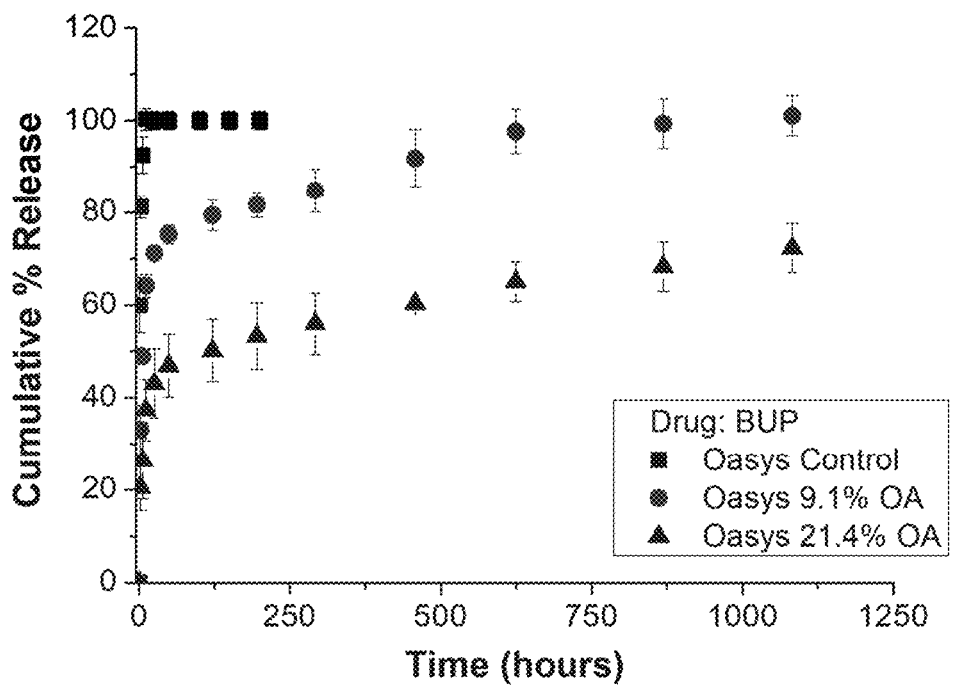
FIG. 4 Cumulative % release of BUP from contact lenses loaded with oleic acid. Oasys® contact lenses.

Example 3. Release Kinetics of Cationic Drug Bupivacaine Hydrochloride (BUP) From Silicone Hydrogel Contact Lenses Loaded With Oleic Acid FIGS. 3 and 4 show the release kinetics of an anesthetic drug, BUP from TruEye® and Oasys®. TruEye® control lenses released 80% of loaded BUP in approximately 5 hours. For TruEye® loaded with oleic acid, TruEye® 13.5% OA lenses released 80% of BUP in 300 hours. Based on the release duration for 80% BUP release, the presence of oleic acid in TruEye® can extend the delivery of BUP by a factor of 60-fold. For TruEye® with 28.6% OA, the lenses have only released approximately 60% of loaded BUP after 450 hours.

For the case of Oasys®, control lenses released 80% of loaded BUP in approximately 2 hours. Oasys® lenses with 9.1% OA released 80% of BUP in 100 hours. This indicates that oleic acid can prolong the release of BUP by a factor of 50-fold in Oasys® lenses. For Oasys® with 21.4% OA, approximately 75% of loaded BUP is released after 450 hours.

The results of this example show that silicone CL modified with anionic boundary charges (oleic acid) extended drug delivery by 50-60 folds.

Example 4. Release Kinetics of Cationic Drug Tetracaine Hydrochloride (THCL) From 1-Day ACUVUE Moist® Contact Lenses Loaded With Oleic Acid A maximum oleic acid loading of 2.9 wt. % was observed for 1-day ACUVUE Moist® contact lenses. Conventional hydrogel contact lenses such as 1-day ACUVUE Moist® do not consist of a hydrophobic region and are predominantly composed of pHEMA hydrophilic polymer. As a result, these lenses have higher water content than silicone hydrogel contact lenses and the lack of hydrophobic silicone domains reduces oxygen permeability and absorption of hydrophobic molecules such as oleic acid.

Figure 5:
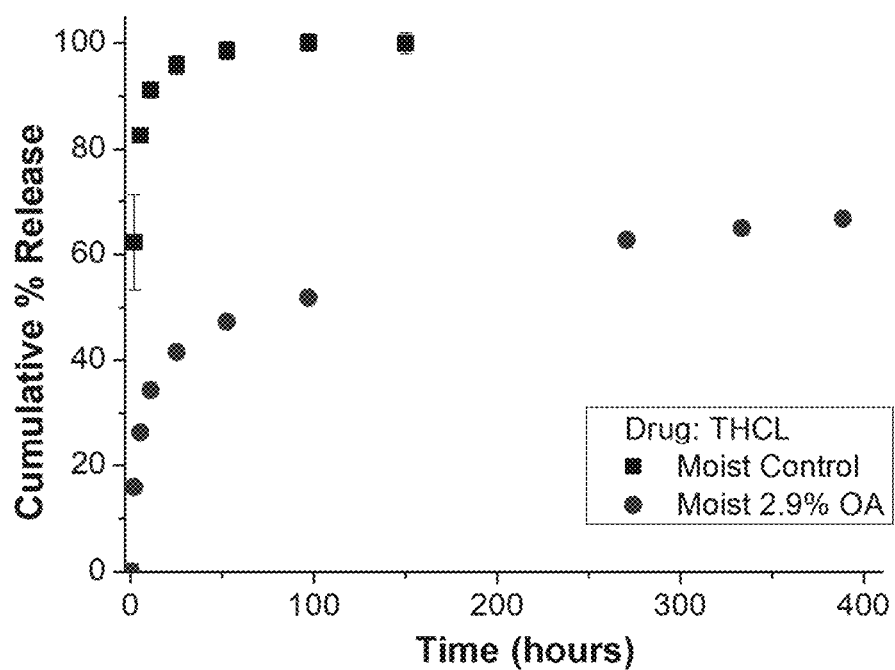
FIG. 5 Cumulative % release of THCL from contact lenses loaded with oleic acid. 1-day ACUVUE Moist® contact lenses.
Figure 6:
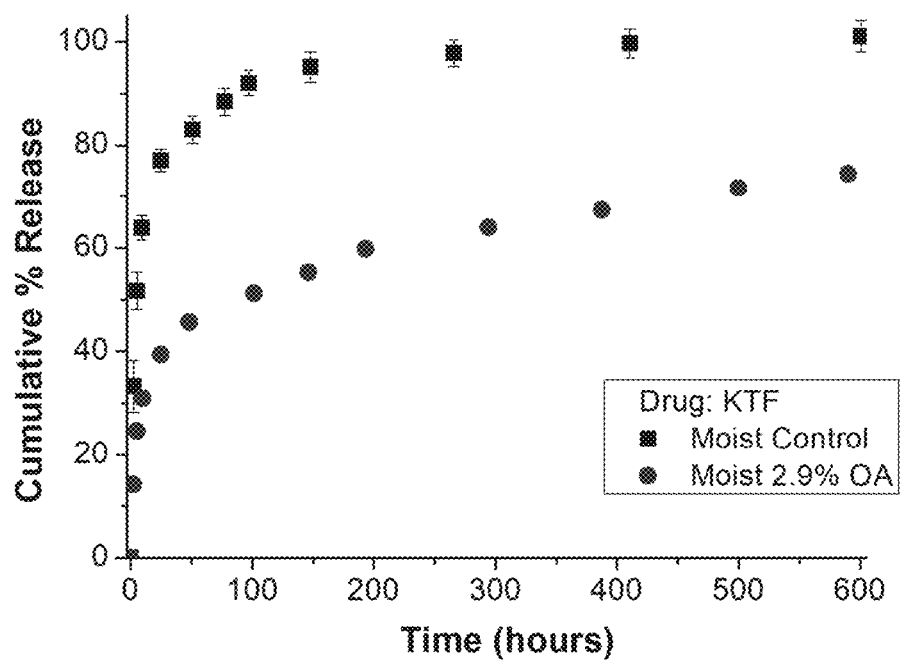
FIG. 6 Cumulative % release of KTF from contact lenses loaded with oleic acid. 1-day ACUVUE Moist® contact lenses.

FIGS. 5 & 6 describes the effect of oleic acid in the release kinetics of KTF and THCL from 1-day ACUVUE Moist® contact lenses. Control lenses released 90% of THCL in less than 24 hours. For lenses loaded with 2.9% OA, 60% of THCL was released after 250 hours.

For KTF (FIG. 5), control lenses released 80% of drug in approximately 48 hours. For the case of lenses loaded with 2.9% OA, 70% of KTF was released after 500 hours.

Therefore, even though the amount of oleic acid loaded in the lenses was limited to 2.9 wt. %, the release extension achieved for THCL and KTF is still significant.

Figure 7:
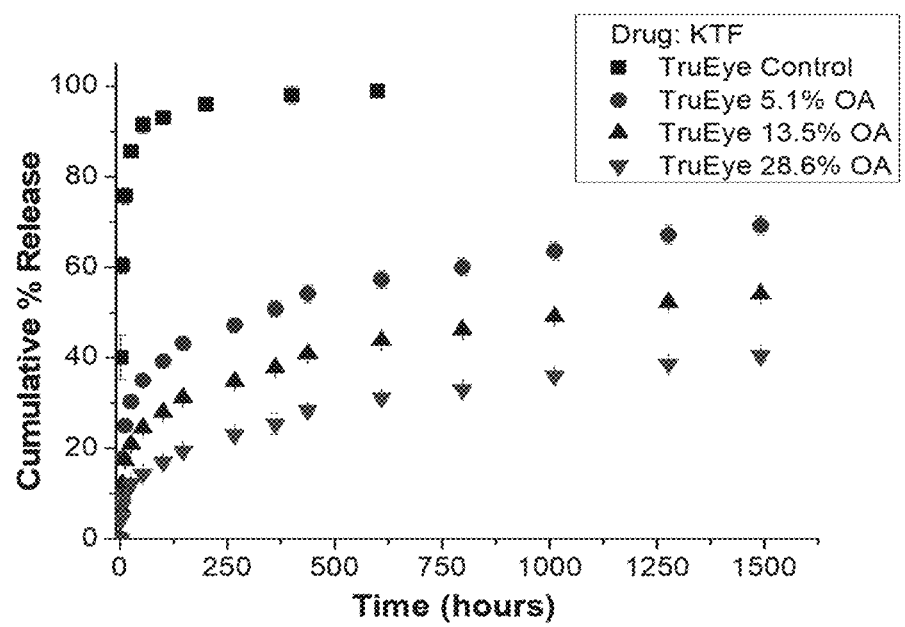
FIG. 7 Cumulative % release of ketotifen fumarate (KTF) from contact lenses loaded with oleic acid. TruEye® contact lenses.
Figure 8:
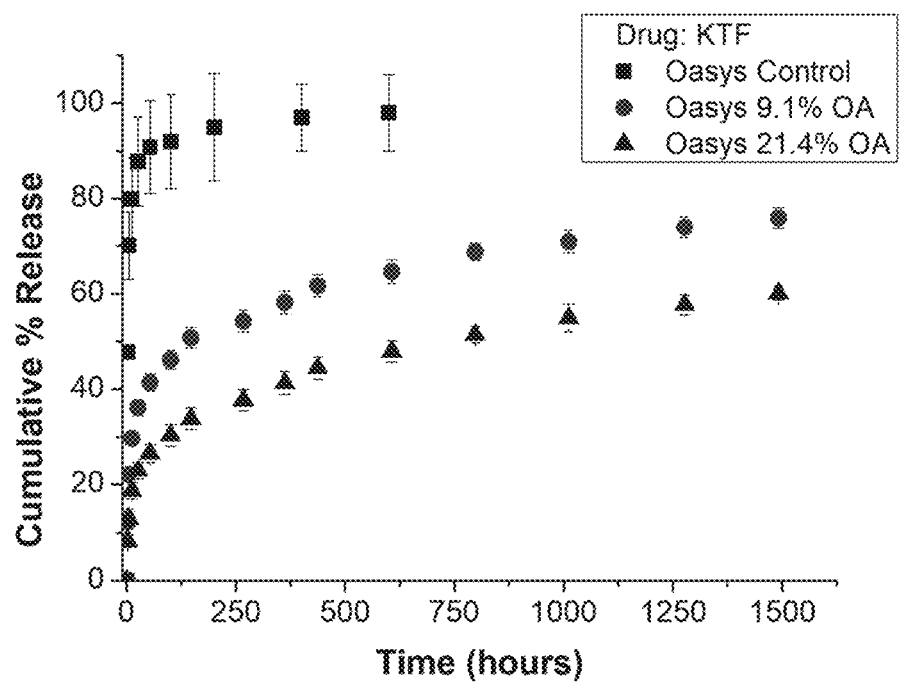
FIG. 8 Cumulative % release of KTF from contact lenses loaded with oleic acid. Oasys® contact lenses.

Example 5. Release Kinetics of Cationic Drug Ketotifen Fumarate (KTF) From Silicone Hydrogel Contact Lenses Loaded With Oleic Acid FIGS. 7 and 8 show the effect of oleic acid on the release kinetics of KTF, a relatively selective, noncompetitive antagonist of the histamine H1 receptor. TruEye® control lenses released 80% of loaded KTF in less than 50 hours. TruEye® lenses loaded with oleic acid released only 40%, 30%, and 18% of loaded KTF after 100 hours for TruEye® 5.1% OA, TruEye® 13.5% OA, and TruEye® 28.6% OA, respectively.

For Oasys®, control lenses also released more than 90% of loaded KTF in less than 50 hours, as with the case of TruEye®. After 100 hours, Oasys® 9.1% OA and Oasys® 21.4% OA released 45% and 30% of loaded KTF, respectively. For both TruEye® and Oasys®, release kinetics were still extended after 1500 hours. The effect of oleic acid was more pronounced with TruEye® than Oasys® lenses.

The results show that boundary surface charge modified silicone-hydrogel lens extended delivery by 30 folds.

Example 6. Release Kinetics of Anionic Drug Diclofenac Sodium (DFNa) From Silicone Hydrogel Contact Lenses Loaded With Sphingolipids or 1,2-dioleoyl-3-trimethylammonium-propane (DOTAP)

This example shows extension of anionic drug delivery by boundary cationic charge modified contact lens.

Figure 9:
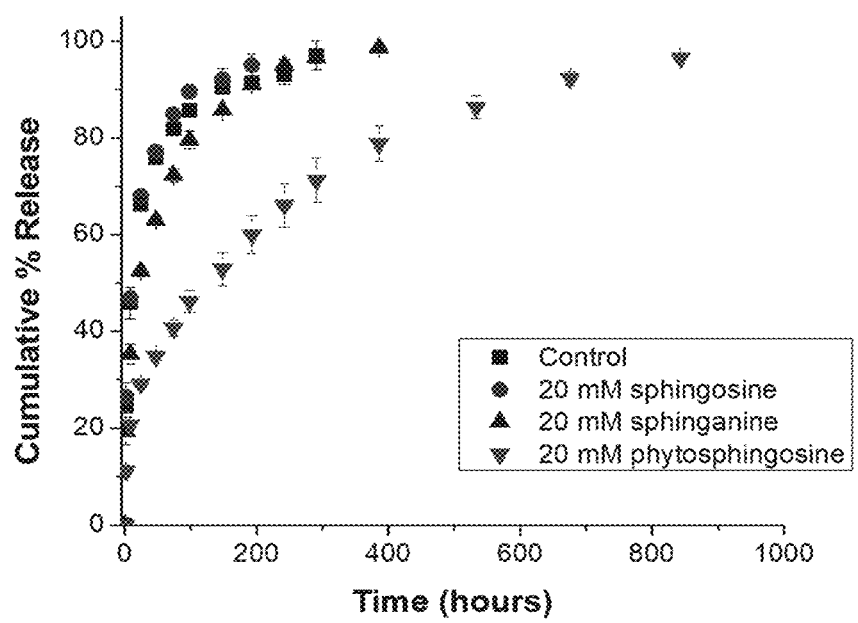
FIG. 9 Cumulative % release of diclofenac sodium (DFNa) from contact lenses loaded with sphingosine, sphinganine, or phytosphingosine. TruEye® contact lenses.

FIG. 9 shows the effect of three sphingolipids (sphingosine, sphinganine, phytosphingosine) on the release kinetics of DFNa, an anionic non-steroidal anti-inflammatory drug. TruEye® control lenses and lenses loaded with sphingosine or sphinganine released 80% of loaded DFNa in less than 100 hours. TruEye® lenses loaded with phytosphingosine released 80% of loaded DFNa in 400 hours.

Figure 10:
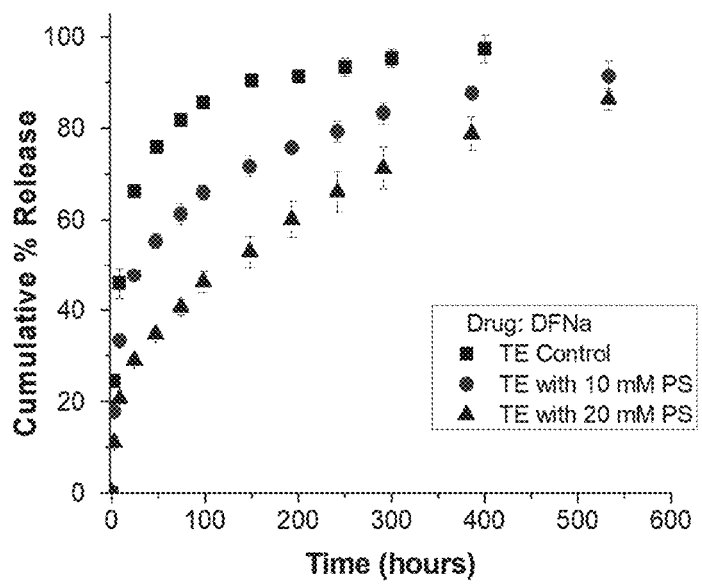
FIG. 10 Cumulative % release of DFNa from unmodified and phytosphingosine (PS) loaded contact lenses. TruEye® contact lenses.
Figure 11:
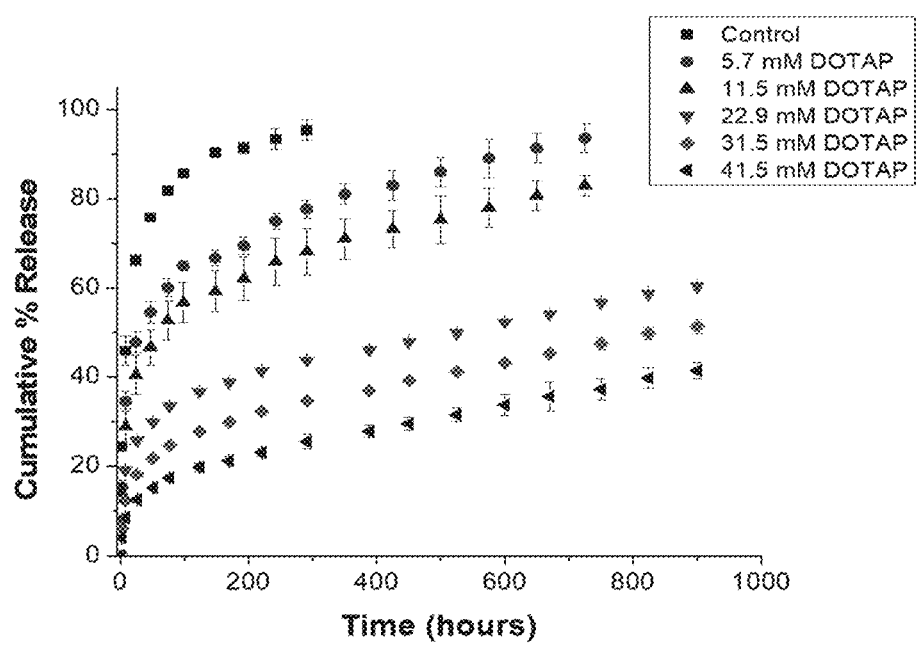
FIG. 11 Cumulative % release of DFNa from contact lenses loaded with 1,2-dioleoyl-3-trimethylammonium propane (DOTAP). TruEye® contact lenses.
Figure 12:
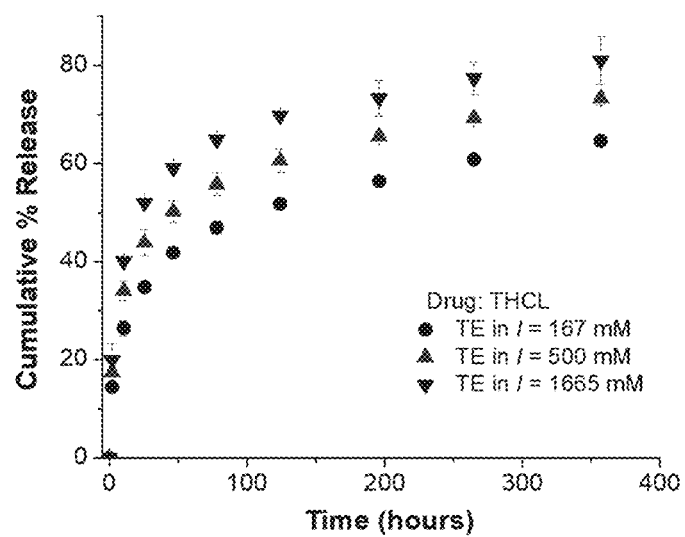
FIG. 12 Cumulative % release of tetracaine hydrochloride (THCL) from contact lenses loaded with oleic acid in phosphate buffer saline at different ionic strength. TruEye® contact lenses.
Figure 13:
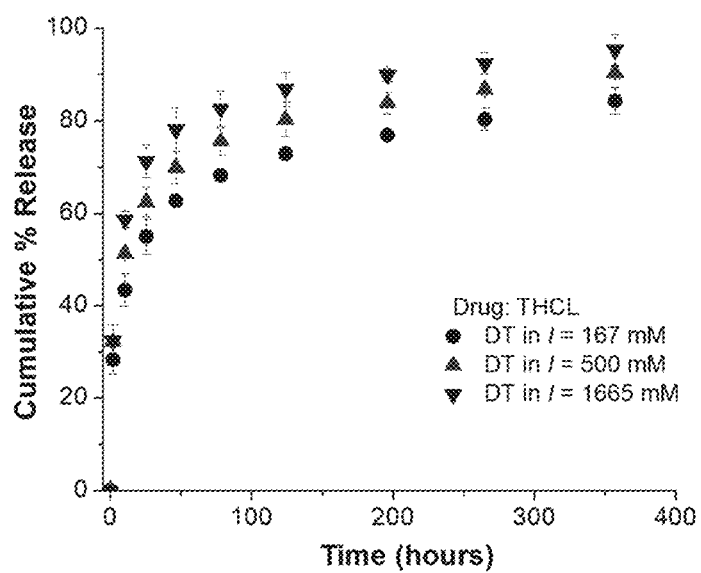
FIG. 13 Cumulative % release of THCL from contact lenses loaded with oleic acid in phosphate buffer saline at different ionic strength. Dailies Total 1® contact lenses.
Figure 14:
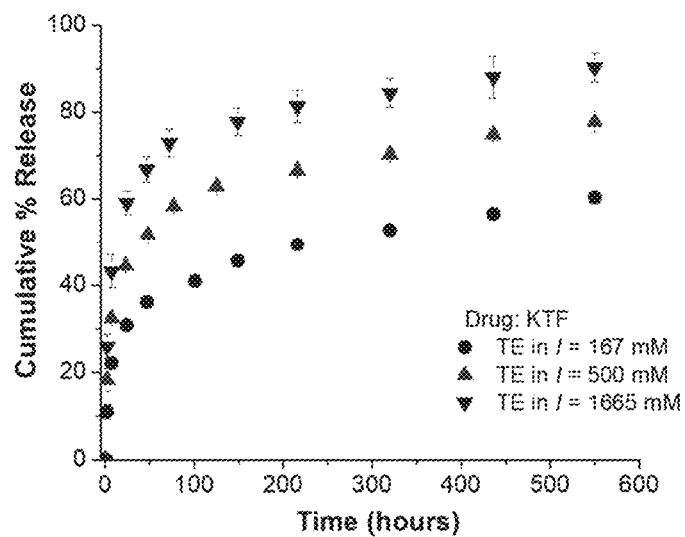
FIG. 14 Cumulative % release of KTF from contact lenses loaded with oleic acid in phosphate buffer saline at different ionic strength. TruEye® contact lenses.
Figure 15:
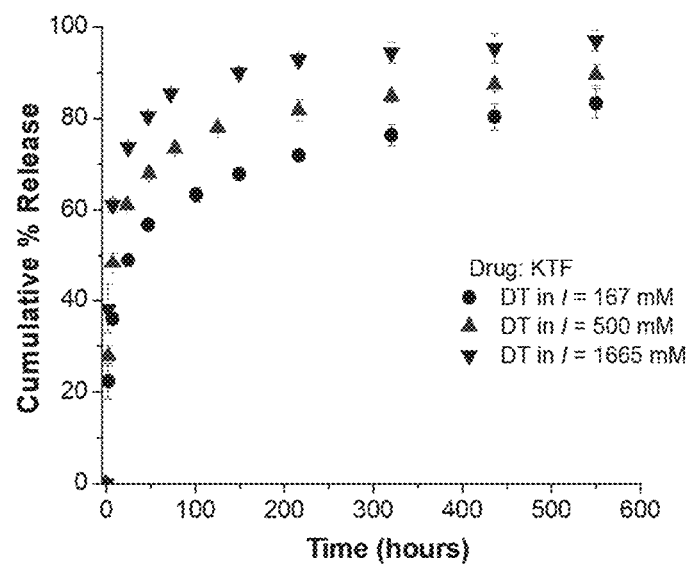
FIG. 15 Cumulative % release of KTF from contact lenses loaded with oleic acid in phosphate buffer saline at different ionic strength. Dailies Total 1® contact lenses.
Figure 16:
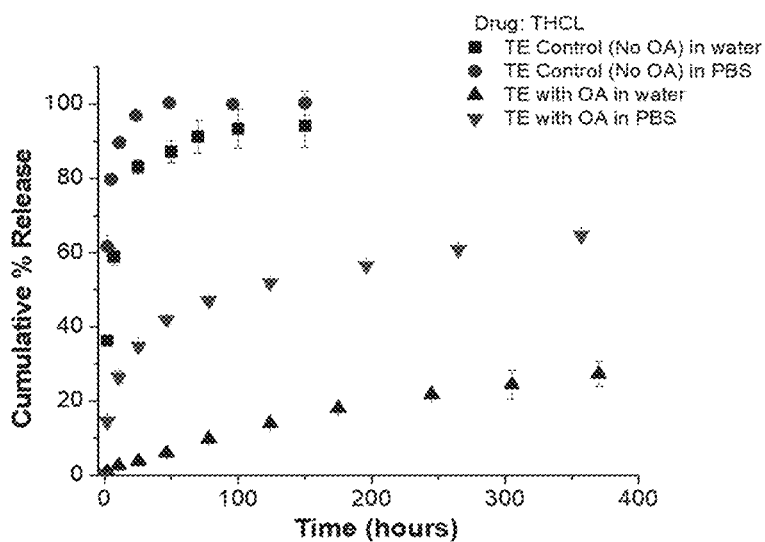
FIG. 16 Cumulative % release of THCL from control contact lenses or lenses loaded with oleic acid. Release in phosphate buffer saline or in deionized water. TruEye® contact lenses.
Figure 17:
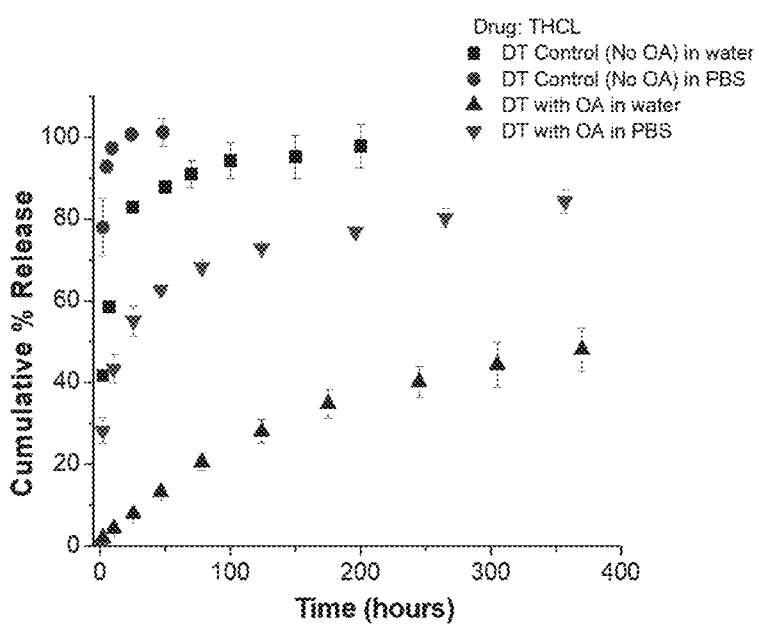
FIG. 17 Cumulative % release of THCL from control contact lenses or lenses loaded with oleic acid. Release in phosphate buffer saline or in deionized water. Dailies Total 1® contact lenses.
Figure 18:
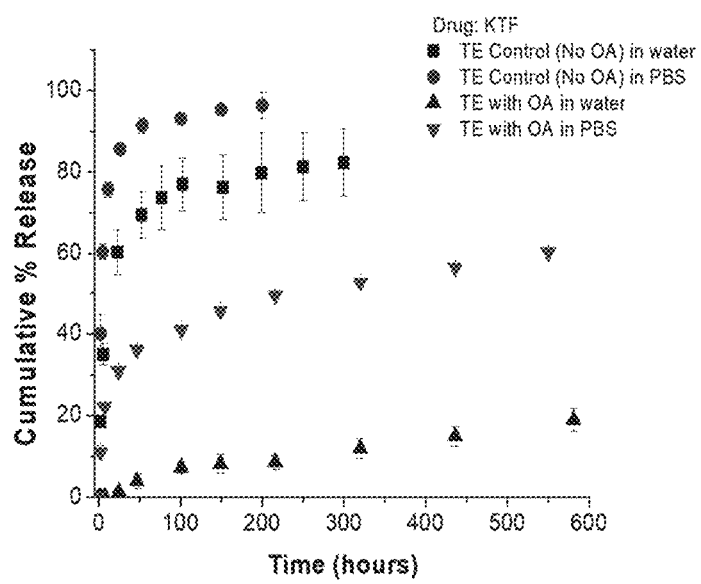
FIG. 18 Cumulative % release of KTF from control contact lenses or lenses loaded with oleic acid. Release in phosphate buffer saline or in deionized water. TruEye® contact lenses.
Figure 19:
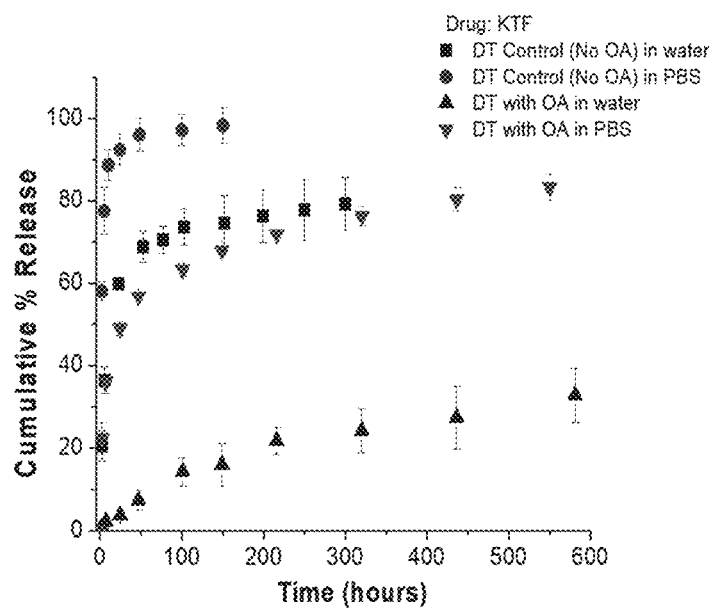
FIG. 19 Cumulative % release of KTF from control contact lenses or lenses loaded with oleic acid. Release in phosphate buffer saline or in deionized water. Dailies Total 1® contact lenses.
Figure 20:
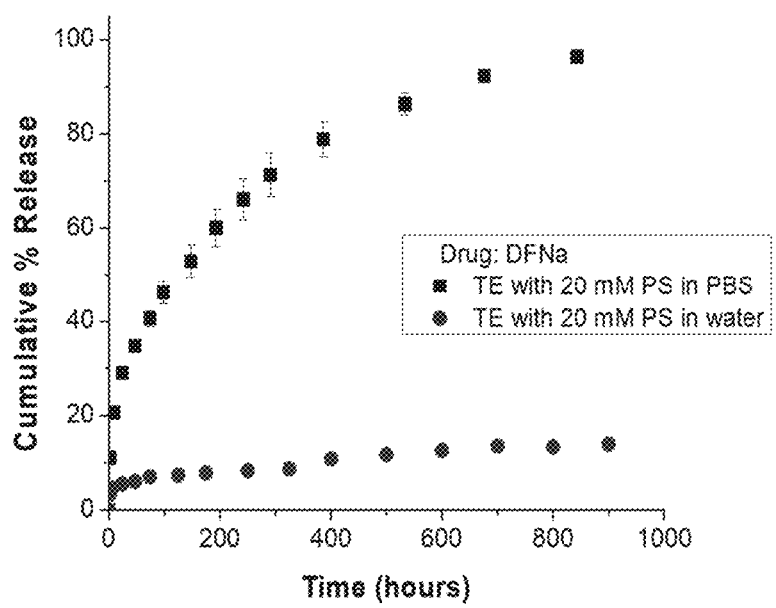
FIG. 20. Cumulative % release of DFNa in PBS or deionized water from contact lenses loaded with 20 mM phytosphingosine (PS). TruEye® contact lenses.

FIG. 10 shows the effect of DOTAP, a cationic lipid, on the release kinetics of DFNa. As the DOTAP-ethanol soaking concentration was increased, the release kinetics of DFNa was more extended. For example, TruEye® control lenses released 80% of loaded DFNa in less than 100 hours, while TruEye® lenses loaded with 5.7 mM DOTAP and 41.5 mM DOTAP released less than 90% and 30% of loaded DFNa after 500 hours, respectively.

Example 7. Effect of Ionic Strength of Release Medium on Release Kinetics of Cationic Drugs Ketotifen Fumarate (KTF) and Tetracaine Hydrochloride (THCL) From Silicone Hydrogel Contact Lenses Loaded With Oleic Acid FIGS. 11, 12, 13 and 14 show the release kinetics of KTF and THCL from TruEye® and Dailies Total 1® contact lenses that was investigated in PBS solutions with different ionic strength (I=167, 500, 1665 mM).

For both lenses, an oleic acid soaking concentration of 15 mg/mL was utilized. At this concentration, the oleic acid weight % was 2.5 and 5.2% (weight of oleic acid/ weight of dry unmodified lens) for ACUVUE TruEye® and Dailies Total 1®, respectively.

TruEye® lenses loaded with oleic acid released 70% of THCL in 100 hours for I=1665 mM, while for I=167 mM and 500 mM lenses released 70% of KTF in more than 200 hours.

Dailies Total 1® lenses loaded with oleic acid releasef 70% of THCL in 75 hrs, 50 hrs and 25 hrs for I=167, 500, and 1665 mM, respectively.

TruEye® lenses loaded with oleic acid released 70% of KTF in 50 hours for I=1665 mM, while for I=167 mM and 500 mM lenses release 70% of KTF in over 200 hours.

Dailies Total 1® lenses loaded with oleic acid released 70% of KTF in 200 hrs, 75 hrs and 15 hrs for I=167, 500, and 1665 mM, respectively.

Example 8. Comparison of Release Kinetics in Water and PBS Solution of Cationic Drugs Ketotifen Fumarate (KTF) and Tetracaine Hydrochloride (THCL) From Silicone Hydrogel Contact Lenses Loaded With Oleic Acid FIGS. 15, 16, 17 and 18 show the release kinetics of KTF and THCL from TruEye® and Dailies Total 1® contact lenses in PBS or in deionized water. We studied both control lenses and lenses loaded with oleic acid. For lenses loaded with oleic acid, an oleic acid soaking concentration of 15 mg/mL was utilized. At this concentration, the oleic acid weight % was 2.5 and 5.2% (weight of oleic acid/ weight of dry unmodified lens) for ACUVUE TruEye® and Dailies Total 1®, respectively.

For both THCL and KTF, less than 10% of loaded drug was released in water after 24 hrs from TruEye® and Dailies Total 1®. TruEye® lenses loaded with oleic acid released THCL and KTF at a nearly constant rate for 400 and 600 hours, respectively. This example demonstrated the exceptional slowing down of drug release into deionized water (with a very low ionic strength) due to the thicker interfacial layer created by the oleic acid anionic charge modification.

Figure 21:
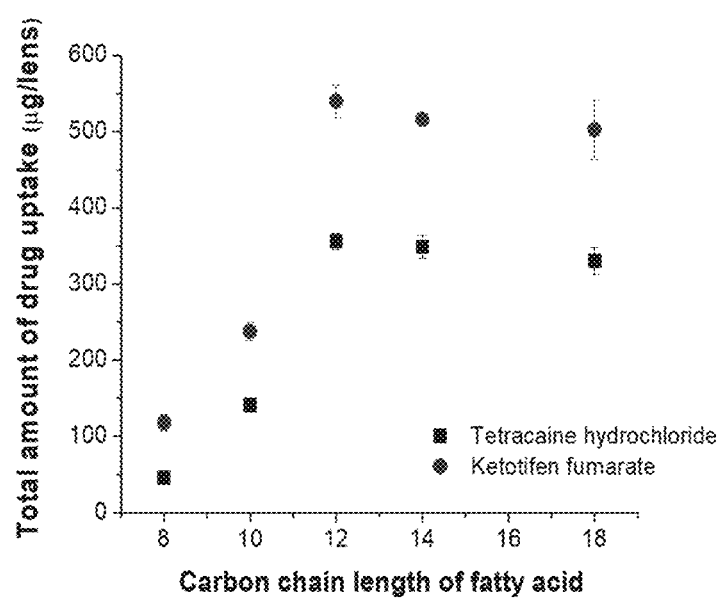
FIG. 21 The total amount of drug uptake as a function of carbon chain length of fatty acid. Fatty acids are loaded in contact lenses at a fixed concentration of 25 mM. TruEye® contact lenses FIG. 22 The total amount of drug uptake as a function of carbon chain length of fatty acid. Fatty acids are loaded in contact lenses at a fixed concentration of 25 mM. Dailies Total 1® contact lenses FIG. 23 Cumulative % release of THCL from contact lenses as a function of fatty acid chain length. TruEye® contact lenses.
Figure 22:
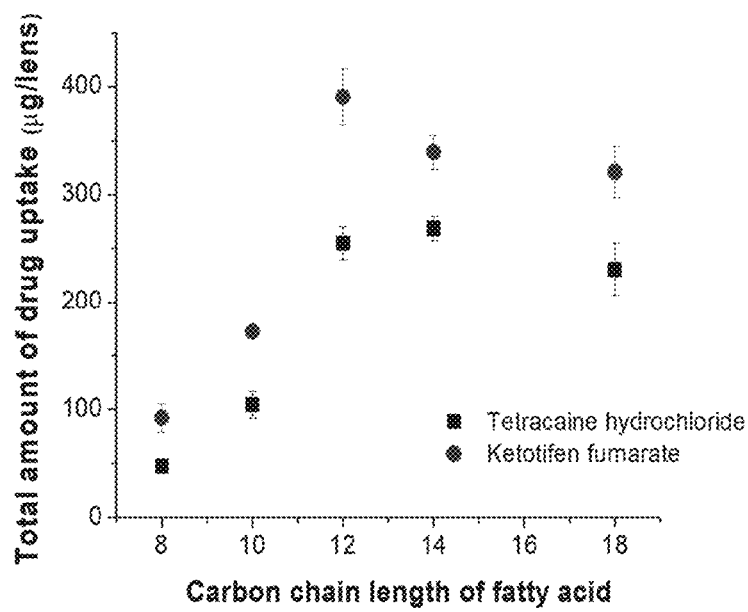
Figure 23:
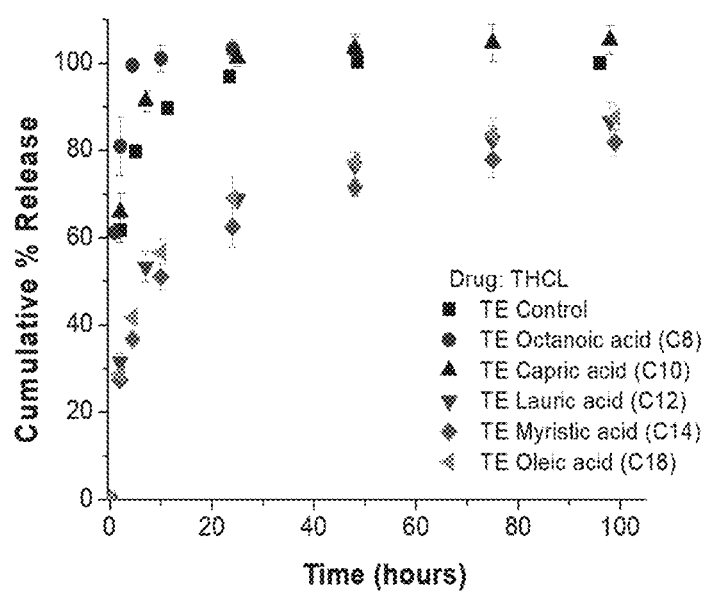
Figure 24:
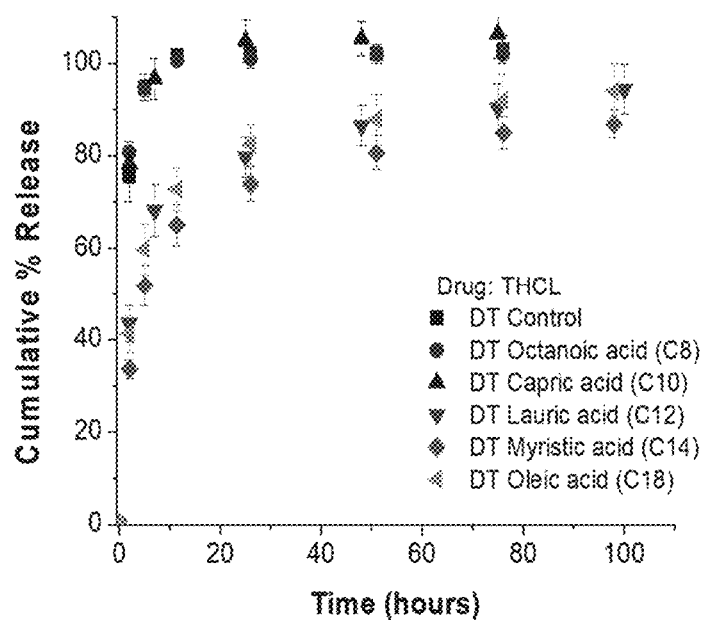
FIG. 24 Cumulative % release of THCL from contact lenses as a function of fatty acid chain length. Dailies Total 1® contact lenses.
Figure 25:
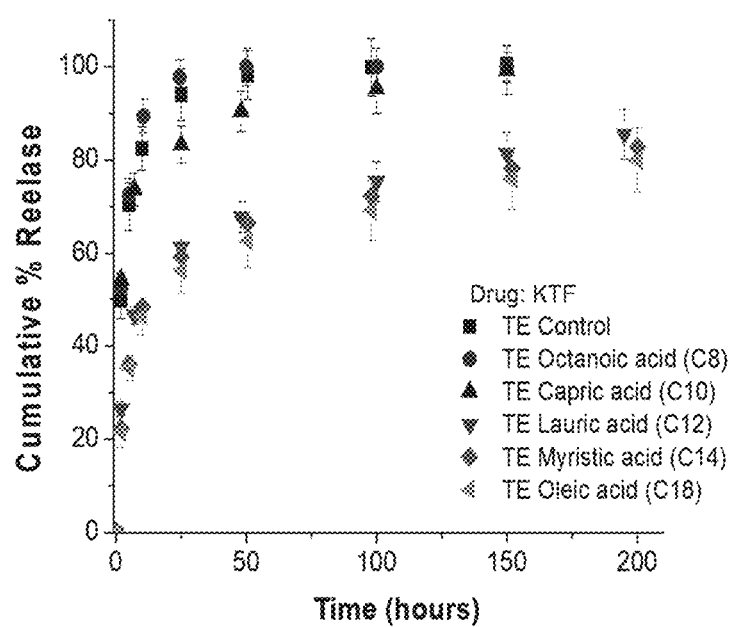
FIG. 25 Cumulative % release of KTF from contact lenses as a function of fatty acid chain length. TruEye® contact lenses.
Figure 26:
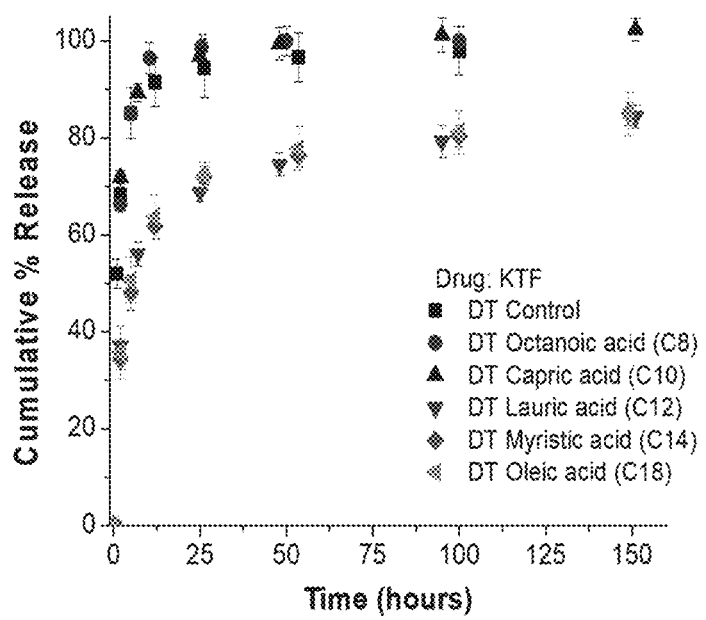
FIG. 26 Cumulative % release of KTF from contact lenses as a function of fatty acid chain length. Dailies Total 1® contact lenses.
Figure 27:
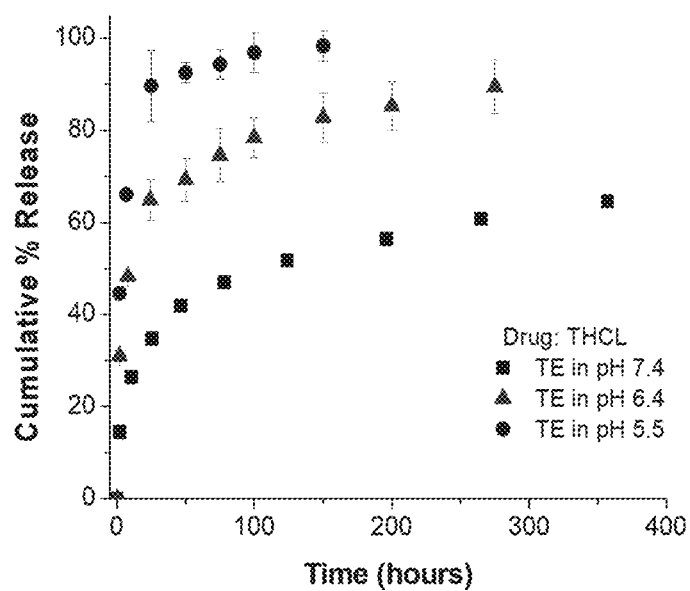
FIG. 27 Cumulative % release of THCL from contact lenses loaded with oleic acid. Release in PBS at different pH values (5.5, 6.4, and 7.4). TruEye® contact lenses.
Figure 28:
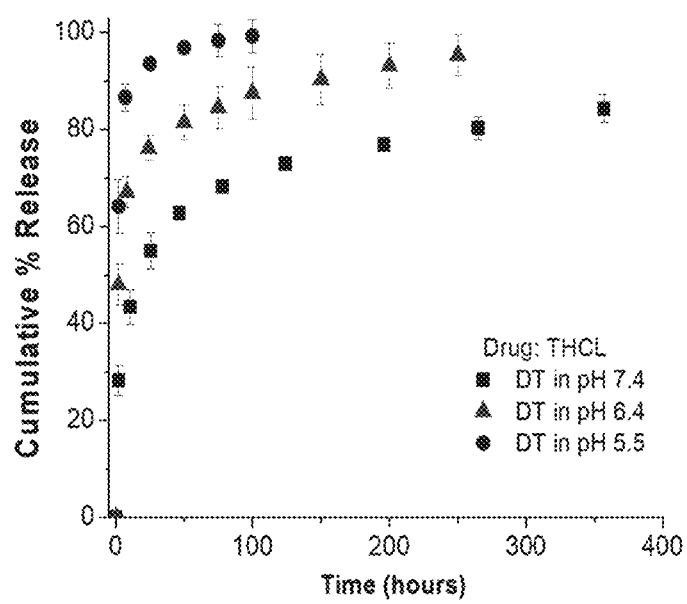
FIG. 28 Cumulative % release of THCL from contact lenses loaded with oleic acid. Release in PBS at different pH values (5.5, 6.4, and 7.4). Dailies Total 1® contact lenses.
Figure 29:
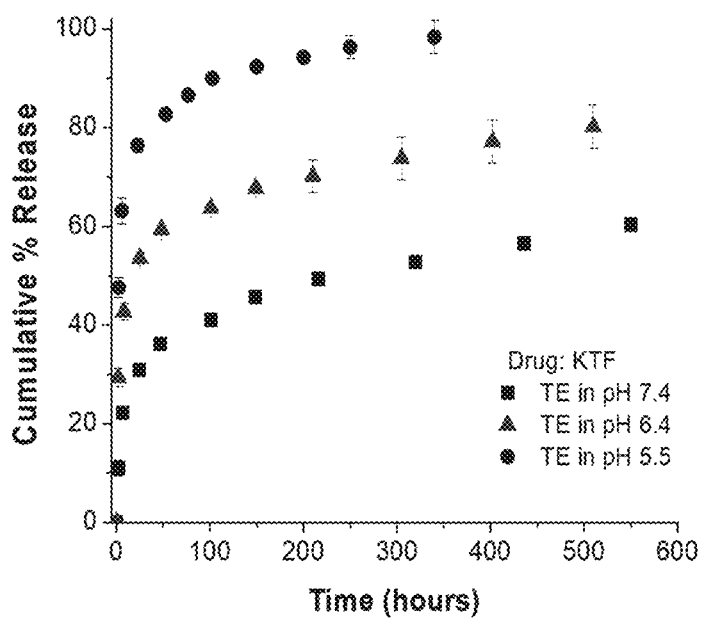
FIG. 29 Cumulative % release of KTF from contact lenses loaded with oleic acid. Release in PBS at different pH values (5.5, 6.4, and 7.4). TruEye® contact lenses.
Figure 30:
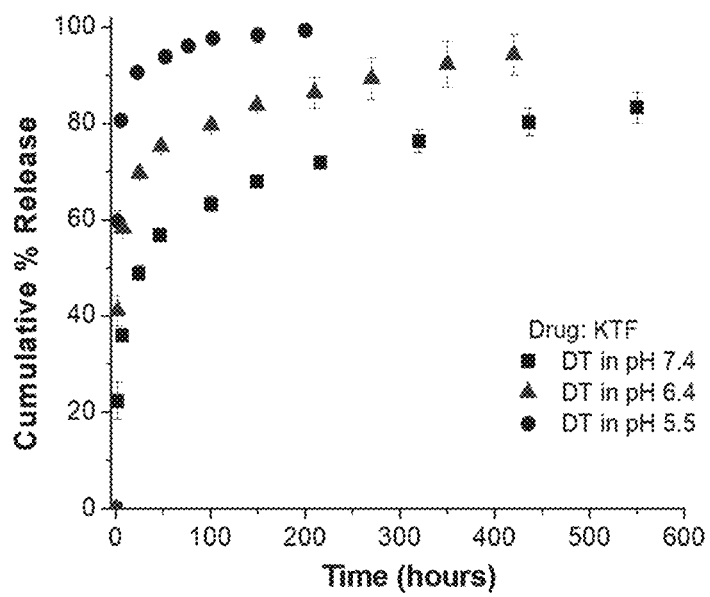
FIG. 30 Cumulative % release of KTF from contact lenses loaded with oleic acid.

Example 9. Comparison of Release Kinetics of Cationic Drugs Ketotifen Fumarate (KTF) and Tetracaine Hydrochloride (THCL) From Silicone Hydrogel Contact Lenses as a Function of Fatty Acid Carbon Chain Length FIGS. 21 and 22 show the uptake of KTF and THCL in TruEye® and Dailies Total 1® contact lenses loaded with fatty acids with different carbon chain lengths. FIGS. 23, 24, 25, and 26 show the corresponding release kinetic profiles of KTF and THCL from TruEye® and Dailies Total 1® contact lenses in PBS. We studied both control lenses and lenses loaded with fatty acids. A fixed fatty acid concentration of 25 mM was used for loading in the lenses. The five fatty acids used were octanoic acid (C=8), capric acid (C=10), lauric acid (C=12), myristic acid (C=14), and oleic acid (C=18).

For both drugs, the uptake was substantially increased when the chain length of the fatty acid was longer than 10. Fatty acids having a chain length shorter than 10 have aqueous solubilities that led to a much lower population density at the pore surface of the lenses and thus, limited their abilities in generating interfacial anionic boundary charges. There is a substantial increase in cationic drug uptake with fatty acids having a chain length longer than 12 due to more anionic boundary charges at the pore interfaces. As expected, it significantly extended the cationic drug release kinetics as shown in FIGS. 23, 24, 25, and 26.

Example 10. Comparison of Release Kinetics in PBS at Different pH Levels of Cationic Drugs Ketotifen Fumarate (KTF) and Tetracaine Hydrochloride (THCL) From Silicone Hydrogel Contact Lenses Loaded With Oleic Acid FIGS. 27, 28, 29 and 30 show the release kinetics of KTF and THCL from TruEye® and Dailies Total 1® contact lenses that was investigated in PBS solutions at different pH levels (pH=5.5, 6.4, and 7.4).

For both lenses, an oleic acid soaking concentration of 15 mg/mL was utilized. At this concentration, the oleic acid weight % was 2.5 and 5.2% (weight of oleic acid/weight of dry unmodified lens) for ACUVUE TruEye® and Dailies Total 1®, respectively.

The release durations of THCL from TruEye® with oleic acid in PBS at a pH of 5.5 and 6.4 are 10 h and 50 h, respectively. On the other hand, the release durations in PBS at the physiological pH are greater than 300 h. For the case of Dailies Total 1® with oleic acid, THCL release durations are 3 h, 10 h, and 100 h in PBS at a pH of 5.5, 6.4, and 7.4, respectively. The release kinetics of KTF is also accelerated as the pH of the release medium decreases from 7.4 to 5.5.

When the pH of the release medium decreases from 7.4 to 5.5, this leads to the protonation of the oleic acid carboxylates and subsequent rapid release of the cationic drug molecules from the lenses. Moreover, the faster release at lower pH could be also attributed to the increase in the solubility of the drugs. For example, the solubility in PBS of ketotifen fumarate at pH 7 and 10 was reported in the literature to be 10.5 and 0.02 mg/mL, respectively. The degree of ionization of KTF and THCL increases at lower pH values, which leads to higher aqueous solubilities in more acidic pH environments.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude the specification.

What is claimed is:

1. A contact lens device comprising cargo molecules embedded in a nanocomposite, wherein the nanocomposite comprises hydrophilic polymer domains, hydrophobic polymer domains, aqueous pores, and boundary charged double layers, wherein: (a) the interfacial domain-pore surface area is from 5 to 500 m²/g device, (b) the aqueous pore volume is 30 to 80% of the total device volume, (c) at least 80% of the cargo molecules partition into the boundary charged double layers formed at the interface of (i) aqueous pores and (ii) either hydrophobic polymer domains or hydrophilic polymer domains, (d) the charged boundary double layers have a surface charge density of 0.005 to 0.5 Coulomb/meter², and (e) the aqueous pores including the cargo molecules have an ionic strength of 0.1 to 100 mM, and osmolarity of 200-300 mM.

2. The device according to claim 1, wherein each of the boundary charged double layers is formed from (i) the charge of a head group of a boundary charge modifier, and (ii) the charge of the cargo molecules or a counter ion to the charged head group, wherein the boundary charge modifier is a molecule having a charged head group and a hydrophobic tail and is immobilized at the boundary charged double layer.

3. The device according to claim 1, wherein the hydrophilic polymer domains are formed from a monomer with logP<1, wherein the monomer comprises one or more hydrophilic groups selected from the group consisting of: hydroxy group, alkyl glycol, amine, lactam, carboxylic group, and sulfonic group.

4. The device according to claim 3, wherein the monomer is 2-hydroxyethyl methacrylate (HEMA), N,N-dimethylacrylamide (DMA), N-vinyl-2-pyrrolidone (NVP), 4,4-dimethyl-2-vinyl-2-oxazolin-5-one, methacrylic acid, N-(hydroxymethyl)acrylamide, N-[3-(dimethylamino)propyl]methacrylamide, or ethylene glycol dimethacrylate.

5. The device according to claim 1, wherein the hydrophobic polymer domains comprise a hydrophobic polymer formed from monomer or oligomer with a logP>3, wherein the monomer comprises one or more hydrophobic groups selected from the group consisting of an alkyl group, an aromatic group, an ester group, and a perfluoroalkyl group.

6. The device according to claim 5, wherein the monomer is 3-[tris(trimethylsiloxy)silyl]propyl methacrylate (TRIS), 3-methacryloxy-2-hydroxypropoxy (propylbis(trimethylsilyloxy) methylsilane (SIGMA), dimethyl siloxane, monomethyl siloxane, fluorosiloxane, or methyl Methacrylate (MMA).

7. The device according to claim 2, wherein the boundary charged modifier is a Bronsted-Lowry acid.

8. The device according to claim 7, wherein the boundary charged modifier is a fatty acid with a carbon chain length of 8-24 and one acid head, and the cargo molecules are positively charged.

9. The device according to claim 8, wherein the boundary charged modifier is oleic acid, linoleic acid, α-linolenic acid, myristic acid, or stearic acid.

10. The device according to claim 2, wherein the boundary charged modifier is a Bronsted-Lowry base.

11. The device according to claim 10, wherein the boundary charged modifier is an alkyl amine, ethanolamine, or a cationic quaternary ammonium salt having a carbon chain length of 8-24 and an alkyl amine, ethanolamine, or quaternary ammonium head group, and the cargo molecules are negatively charged.

12. The device according to claim 11, wherein the boundary charged modifier is sphingosine, sphinganine, or phytosphingosine, or 1,2-dioleoyl-3-trimethylammonium propane.

13. The device according to claim 1, wherein the aqueous pores comprise one or more compounds that are hydrophilic and nonionic.

14. The device according to claim 13, wherein the one or more compounds are selected from the group consisting of: glycerol, polyethylene glycol, polyvinylpyrrolidone, glycoside, and carboxymethylcellulose.

15. The device according to claim 1, wherein the nanocomposite is a transparent nanocomposite.

16. The device according to claim 1, wherein each of the hydrophilic polymer domains and the hydrophobic polymer domains has a diameter or a shortest axis among the three principal axes of an ellipsoidal shaped domain, from 5 to 50 nanometer.

17. A storage package comprising the device of claim 1 and a storage fluid having an ionic strength ≤10% of the ionic strength of the aqueous pores of the device.

18. A method of releasing cargo molecules from a device, comprising the steps of:
- removing the device from the storage package of claim 17,
- placing the device in an aqueous fluid comprising an ionic strength of at least 110 mM, and
- releasing the cargo to the aqueous fluid triggered by the increase of ionic strength from the aqueous pores to the aqueous fluid.

19. The method of claim 18, wherein the aqueous fluid comprises tears.

\* \* \* \* \*